(12) United States Patent  (10) Patent No.: US 8,292,962 B2
Gornet et al.  (45) Date of Patent: Oct. 23, 2012

(54) SPINAL NUCLEUS REPLACEMENT IMPLANTS

(75) Inventors: Matthew Gornet, Chesterfield, MO (US); Thomas Carls, Memphis, TN (US); Jason Eckhardt, Memphis, TN (US); Erica Gray, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 586 days.

(21) Appl. No.: 12/397,412

(22) Filed: Mar. 4, 2009

(65) Prior Publication Data

US 2010/0228350 A1  Sep. 9, 2010

(51) Int. Cl.
    *A61F 2/44* (2006.01)
(52) U.S. Cl. .................................................. 623/17.16
(58) Field of Classification Search .............. 623/17–20; 606/255, 279
    See application file for complete search history.

(56) References Cited

U.S. PATENT DOCUMENTS

| | | | |
|---|---|---|---|
| 4,777,947 A | 10/1988 | Zwick | |
| 4,936,848 A | 6/1990 | Bagby | |
| 5,059,193 A | 10/1991 | Kuslich | |
| 5,250,061 A | 10/1993 | Michelson | |
| 5,458,611 A | 10/1995 | Resnick et al. | |
| 5,472,010 A | 12/1995 | Gonzalez | |
| 5,645,596 A | 7/1997 | Kim et al. | |
| 5,743,918 A | 4/1998 | Calandruccio et al. | |
| 5,888,226 A | 3/1999 | Rogozinski | |
| 6,120,509 A | 9/2000 | Wheeler | |
| 6,346,101 B1 | 2/2002 | Alfano et al. | |
| 6,478,822 B1 | 11/2002 | Leroux et al. | |
| 6,638,310 B2 | 10/2003 | Lin et al. | |
| 6,652,534 B2 | 11/2003 | Zucherman et al. | |
| 6,733,531 B1 | 5/2004 | Trieu | |
| 6,733,534 B2 | 5/2004 | Sherman | |
| 6,749,608 B2 | 6/2004 | Garito et al. | |
| 6,794,960 B2 | 9/2004 | Chiu et al. | |
| 7,001,433 B2 | 2/2006 | Songer et al. | |
| 7,267,692 B2 | 9/2007 | Fortin et al. | |
| 7,615,079 B2* | 11/2009 | Flickinger et al. | 623/17.16 |
| 7,655,026 B2* | 2/2010 | Justis et al. | 606/259 |
| 2002/0120283 A1 | 8/2002 | Holmes | |
| 2002/0156528 A1 | 10/2002 | Gau | |
| 2003/0023308 A1 | 1/2003 | Leroux et al. | |
| 2003/0135277 A1* | 7/2003 | Bryan et al. | 623/17.12 |

(Continued)

FOREIGN PATENT DOCUMENTS

CA    2441384 A1    11/2002

(Continued)

OTHER PUBLICATIONS

Alvin H. McKenzie, MD, Fernstorm Intervertebral Disc Arthroplasty: A Long-Term Evaluation, Orthopedics International Ed., Jul./Aug. 1995, vol. 3, No. 4.

(Continued)

*Primary Examiner* — David Isabella
*Assistant Examiner* — Randy Shay

(57) ABSTRACT

An intervertebral prosthesis implantable within a disc space and disposed between upper and lower vertebral endplates is provided. The prosthesis comprises a plurality of prosthesis components insertable into the disc space, wherein the components have at least one set of complementarily-shaped and sized surfaces, and wherein the at least one set of complementarily-shaped surfaces comprises a slot, and a rod that fits in the slot. A method of implanting an intervertebral prosthesis according to the present invention also is provided.

13 Claims, 5 Drawing Sheets

U.S. PATENT DOCUMENTS

| | | |
|---|---|---|
| 2003/0204261 A1 | 10/2003 | Eisermann et al. |
| 2003/0220691 A1 | 11/2003 | Songer et al. |
| 2004/0024461 A1 | 2/2004 | Ferree |
| 2004/0030391 A1 | 2/2004 | Ferree |
| 2004/0093082 A1 | 5/2004 | Ferree |
| 2004/0176773 A1 | 9/2004 | Zubok et al. |
| 2004/0186576 A1 | 9/2004 | Biscup et al. |
| 2005/0015151 A1 | 1/2005 | Fortin et al. |
| 2005/0149188 A1 | 7/2005 | Cook et al. |
| 2005/0283245 A1* | 12/2005 | Gordon et al. ............. 623/17.15 |
| 2006/0030857 A1* | 2/2006 | de Villiers et al. ............. 606/90 |
| 2006/0095132 A1 | 5/2006 | Kirschman |
| 2006/0106462 A1 | 5/2006 | Tsou |
| 2006/0224240 A1 | 10/2006 | Allard et al. |
| 2007/0050036 A1* | 3/2007 | Felt et al. ...................... 623/17.16 |
| 2007/0198090 A1* | 8/2007 | Abdou ...................... 623/17.11 |
| 2007/0282448 A1* | 12/2007 | Abdou ...................... 623/17.15 |
| 2008/0039843 A1* | 2/2008 | Abdou ........................... 606/61 |
| 2008/0071377 A1* | 3/2008 | Conner et al. ............. 623/17.16 |
| 2008/0086127 A1 | 4/2008 | Patterson et al. |
| 2008/0154382 A1* | 6/2008 | de Villiers et al. ......... 623/17.16 |
| 2008/0208343 A1* | 8/2008 | Felt ............................ 623/17.16 |
| 2008/0287955 A1* | 11/2008 | Michelson ...................... 606/90 |
| 2009/0125112 A1* | 5/2009 | Robinson et al. ........... 623/17.16 |
| 2009/0138053 A1* | 5/2009 | Assell et al. .................. 606/301 |
| 2009/0182343 A1* | 7/2009 | Trudeau et al. .............. 606/102 |
| 2009/0270989 A1* | 10/2009 | Conner et al. ............ 623/17.16 |
| 2010/0185287 A1* | 7/2010 | Allard et al. ................ 623/17.11 |
| 2010/0185288 A1* | 7/2010 | Carls et al. .................. 623/17.11 |
| 2011/0125158 A1* | 5/2011 | Diwan et al. ..................... 606/93 |

FOREIGN PATENT DOCUMENTS

| | | |
|---|---|---|
| DE | 2804936 A1 | 8/1979 |
| EP | 1354572 A2 | 10/2003 |
| WO | WO9531948 | 11/1995 |
| WO | WO02087480 A1 | 11/2002 |
| WO | WO03024368 A1 | 3/2003 |
| WO | WO03099172 A1 | 12/2003 |
| WO | WO2005081884 A2 | 9/2005 |
| WO | WO2005086067 A1 | 9/2005 |

OTHER PUBLICATIONS

Dept. of Surgery, "Arthoplasty with Intercorporal Endoprothesis in Herniated Disc and in Painful Disc," Uddevalla, Sweden, Suppl. 357, 1966.

Hjalmar Reitz and Mauritius J. Joubert, "Intractable Headache and Cervico-Brachialgia Treated by Complete Replacement of Cervical Intervertebral Discs with a Metal Prothesis, Reprinted from the S.A. Medical Journal", vol. 38, Nov. 7, 1964, pp. 881-884.

Lippincott Williams & Wilkins, Inc., "Intervertebral Disc Protheses", Guyer and Ohnmeiss, Spine vol. 28, No. 15S, Copyright 2003, pp. S15-S23.

Medtronic Sofamor Danek, USA, Inc., "Satellite Interdiscal Stabilization Sphere Surgical Technique", 2004, 5 pages.

* cited by examiner

SPINAL NUCLEUS REPLACEMENT IMPLANTS

FIELD OF INVENTION

The present invention is directed to spinal nucleus replacement implants, and systems and methods for implanting the nucleus replacement implants.

BACKGROUND

This disclosure is related to application Ser. No. 12/356,702, Ser. No. 12/356,713, and Ser. No. 12/356,743, each of which is hereby incorporated by reference in their entireties.

The present disclosure relates generally to devices and methods for relieving disc degeneration or injury, and more particularly, to devices and methods for augmenting or replacing a nucleus pulposus. Within the spine, the intervertebral disc functions to stabilize and distribute forces between vertebral bodies. The intervertebral disc comprises a nucleus pulposus which is surrounded and confined by the annulus fibrosis (or annulus).

Intervertebral discs are prone to injury and degeneration. For example, herniated discs typically occur when normal wear, or exceptional strain, causes a disc to rupture. Degenerative disc disease typically results from the normal aging process, in which the tissue gradually loses its natural water and elasticity, causing the degenerated disc to shrink and possibly rupture.

Intervertebral disc injuries and degeneration may be treated by fusion of adjacent vertebral bodies or by replacing the intervertebral disc with a prosthetic. To maintain as much of the natural tissue as possible, the nucleus pulposus may be supplemented or replaced while maintaining all or a portion of the annulus.

It would be advantageous to keep any incision in the annulus minimal, in order to avoid injuring healthy tissue. Accordingly, it is desirable to provide a prosthetic device that requires a relatively small opening or incision in the annulus when being inserted into the disc space.

SUMMARY OF THE INVENTION

An intervertebral prosthesis implantable within a disc space and disposed between upper and lower vertebral endplates is provided. The prosthesis comprises a plurality of prosthesis components insertable into the disc space, wherein the components have at least one set of complementarily-shaped and sized surfaces, and wherein the at least one set of complementarily-shaped surfaces comprises a slot, and a rod that fits in the slot. The components have surfaces configured to engage within the disc space in a manner such that the components form an assembled prosthesis of a size substantially preventing it from being outwardly expelled from the disc space through an opening in the disc space, and the components have bearing surfaces slidably engageable with the endplates to permit articulation between upper and lower vertebral endplates.

In certain embodiments, the prosthesis has a lower surface that is relatively flat. In some embodiments, the prosthesis has an upper surface that comprises a generally hemispherically-shaped surface. In some embodiments, the prosthesis has a lower surface that comprises a generally hemispherically-shaped surface. Also, in certain embodiments, the prosthesis is configured such that in its final shape, it is generally pear shaped.

In some embodiments, when the prosthesis is in its final shape, the plurality of components are locked together with a locking mechanism. Typically, each component of the prosthesis can be inserted into the disc space by being inserted through an opening in the annulus between the upper and lower vertebral endplates.

According to the invention, each of the multiple components has an insertion rod attached to the component for inserting the respective component to which the insertion rod is attached into the disc space. In such embodiments, a first insertion rod of a first component has a slot in which at least a second insertion rod of a second component can be inserted and used to guide the at least second component into the disc space. Typically, the insertion rods are configured such that each can be detached from their respective components.

A method of implanting an intervertebral prosthesis within a disc space between upper and lower vertebral endplates also is provided. In some methods, the prosthesis comprises at least a first component and a second component, and the method comprises using a first insertion rod attached to the first component to insert the first component through an incision in an annular wall and into the disc space, using a second insertion rod attached to the second component to insert the second component through the incision in the annular wall and into the disc space, and after the first component and second component are in their respective final positions in the disc space, detaching the first and second insertion rods from their respective components.

In certain methods according to the present invention, wherein prior to insertion through the annular wall and into the disc space, the method of implanting an intervertebral prosthesis further comprises rotating at least one of the components approximately 90 degrees so that the at least one component is inserted through the incision and into the disc space in a vertical position. With using such methods, the at least one component may be rotated approximately 90 degrees back to its original, more horizontal position that has less of a vertical profile.

In some methods according to the present invention, the first insertion rod has a slot and the second insertion rod fits in the slot to enable the second component to cooperate with the first component and be guided into a desired location in the disc space. Also, in certain methods, after the first and second insertion rods are detached from their respective components, the insertion rods may be removed from the disc space and the body.

Additional aspects and features of the present disclosure will be apparent from the detailed description and claims as set forth below.

DETAILED DESCRIPTION

Figure 1:
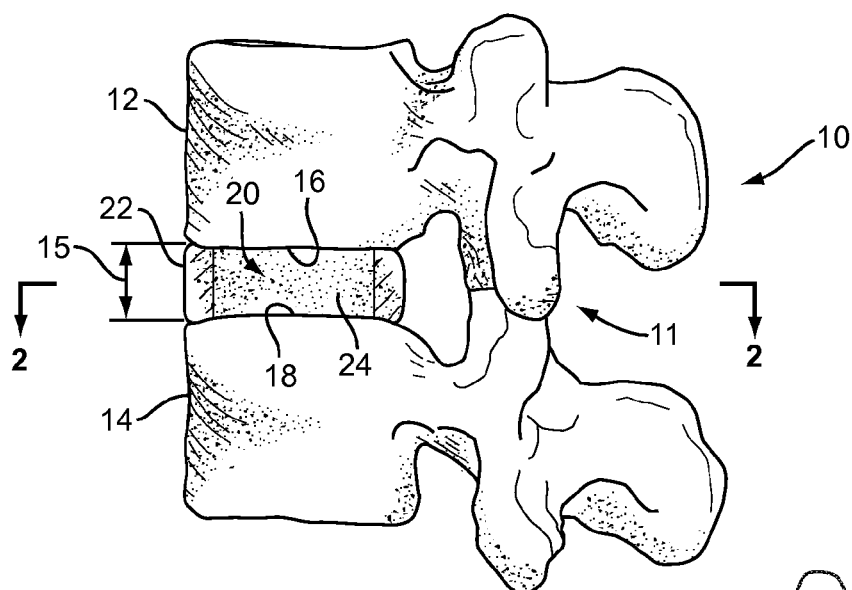
FIG. 1 is a cross-sectional lateral view of a section of a spinal column.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring first to FIG. 1, the reference numeral 10 refers to a vertebral joint section or a motion segment of a vertebral column. The joint section 10 includes adjacent vertebral bodies 12 and 14. The vertebral bodies 12 and 14 include endplates 16 and 18, respectively. An intervertebral disc space 20 is located between the endplates 16 and 18, and an annulus fibrosus 22 surrounds the space 20. In a healthy joint, the space 20 contains a nucleus pulposus 24 within the disc space 20, which helps maintain the distance between endplates 16 and 18, known as the disc height 15. Proper disc height 15 may vary for a particular patient, but medical experts understand how to determine a range of desired disc height 15. The nucleus pulposus 24 may degenerate with age, disease or trauma, permitting the endplates 16 and 18 to move closer together.

Figure 2:
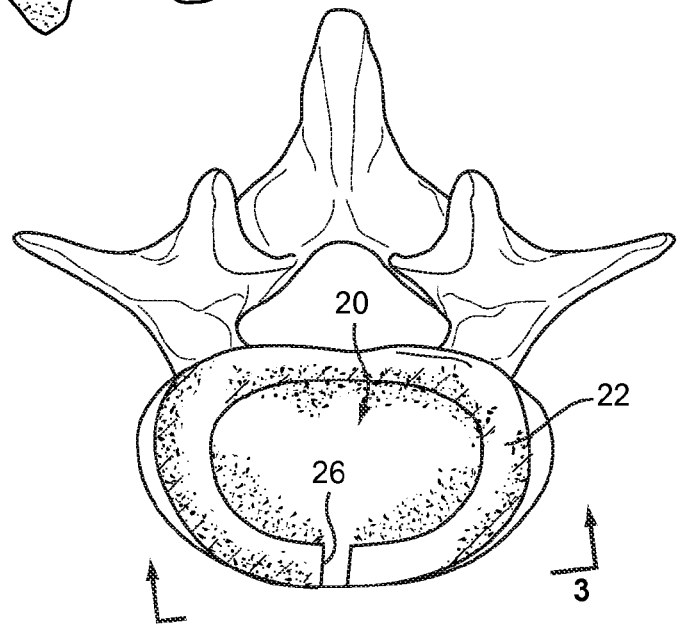
FIG. 2 is an exemplary disc incision in the anterior wall of an annulus fibrosus.
Figure 3:
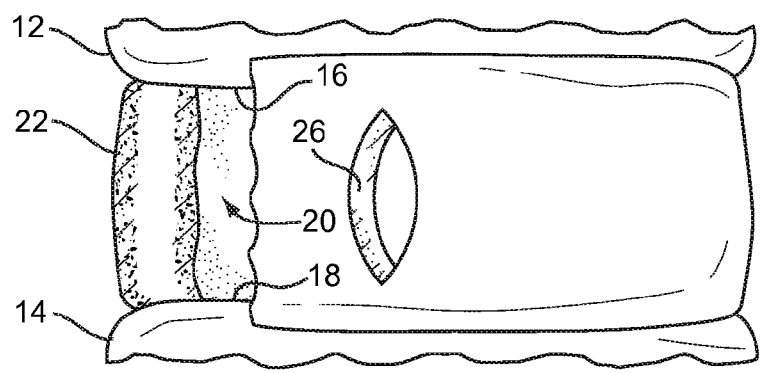
FIG. 3 is a cut-away, cross-sectional view of the layer of spinal column of FIG. 2.

Referring now to FIGS. 2 and 3, an exemplary disc incision 26 is shown in the anterior wall of the annulus fibrosus 22. Disc incision 26 breaches the annulus fibrosus 22 to the disc space 20. As necessary, nucleus pulposus 24 may be removed from the disc space 20 in order to accommodate the insertion of a prosthesis. Illustratively (representatively shown empty in FIG. 2), the disc incision 26 is longitudinal in order to attempt to minimize trauma to the annulus fibrosus 22. The anterior wall of the annulus fibrosus 22 is shown, but the depicted procedure and device are not limited by the example. The particular surgical professional performing the procedure may choose to enter the annulus fibrosus 22 from anterior oblique, posterior, posterior oblique, lateral, transforaminal, or any other approach judged suitable with regard to other factors. The particular surgical professional also may choose to orient the disc incision 26 differently.

A dilator may be used to dilate the disc incision 26, making it large enough to deliver the implant to replace or augment the disc nucleus. The dilator may stretch the disc incision 26 temporarily and avoid tearing so that the disc incision 26 can return back to its undilated size after the dilator instrument is removed. Although some tearing or permanent stretching may occur, the dilation may be accomplished in a manner that allows the disc incision 26 to return to a size smaller than the dilated size after the implantation is complete.

Figure 4:
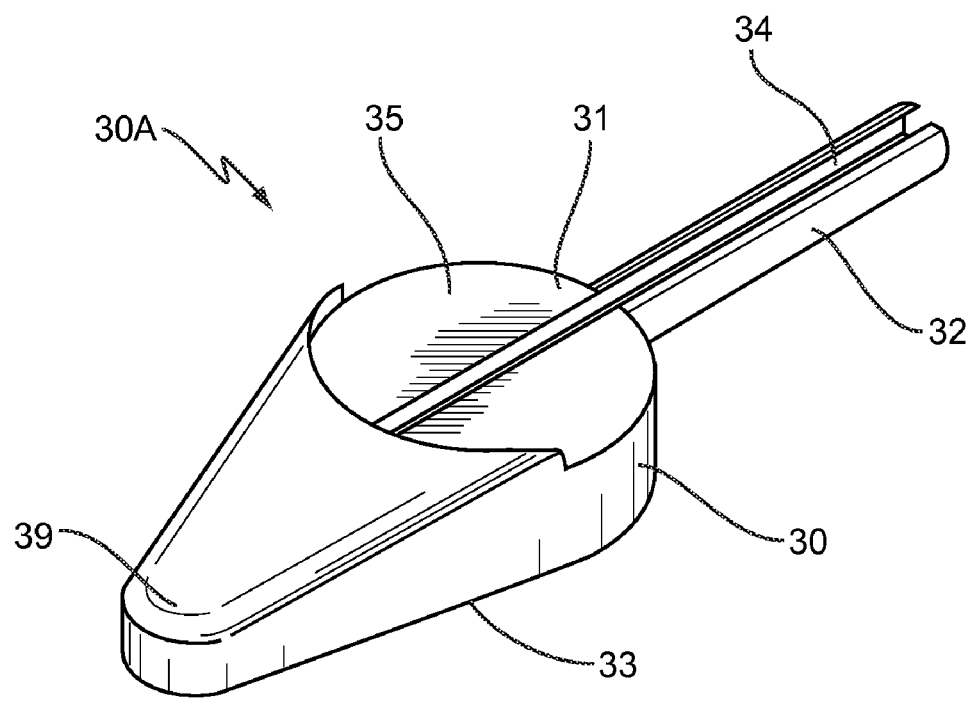
FIG. 4 shows an isometric view of a first module of a prosthesis according to the present invention.

FIGS. 4-8 show various isometric views of a specially designed prosthesis 100 embodying principles of the present invention. FIG. 4 shows a first module 30A, which comprises a first component 30 and a first insertion rod 32. The first component 30 has a cross section that is generally pear-shaped, having a round portion at its proximal end 31 and a pointed portion at its distal end 39. The first component 30 has a relatively flat base or lower surface 33. The first component 30 also has a cut-away portion 35, which has a generally circular shape, at the proximal end 31 of its upper surface. The first insertion rod 32 and the cut-away portion 35 of the first component 30 each contain a slot 34 that is co-linear as it extends through the first insertion rod 32 and through the cut-away portion 35. As shown in FIG. 4, the slot 34 is centered in the middle of the first insertion rod 32 and in the upper surface of the first insertion rod 32. Similarly, as shown in FIG. 4, the slot 34 is centered in the middle of the cut-away portion 35 of the first component 30, and the slot is continuous through both the first insertion rod 32 and the cut-away portion 35.

Figure 5:
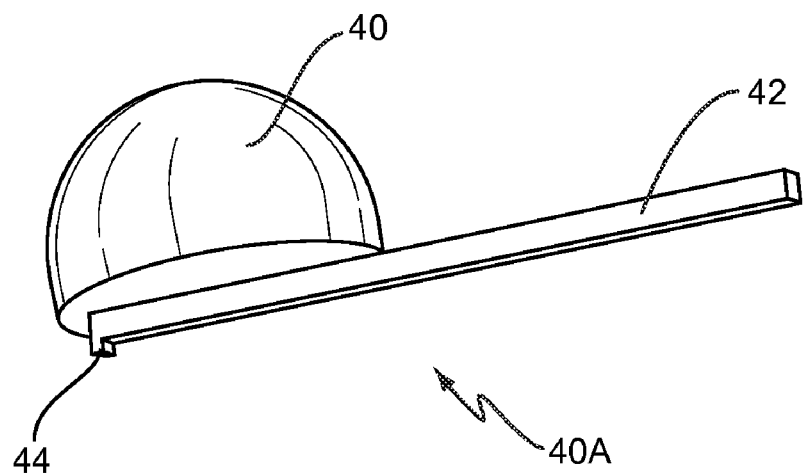
FIG. 5 shows an isometric view of a second module of a prosthesis according to the present invention.

FIG. 5 shows a second module 40A, which comprises a second component 40 and a second insertion rod 42. The second component 40 has an overall shape that is generally hemispherical, with a cross section that is generally circular. In accordance with the invention, the second component 40 is intended to cooperate with or mate with the first component 30. As shown in FIG. 5, the second insertion rod 42 of second module 40 is shaped so that it can cooperate, or fit within, and slide along slot 34 of first insertion rod 32.

Figure 6:
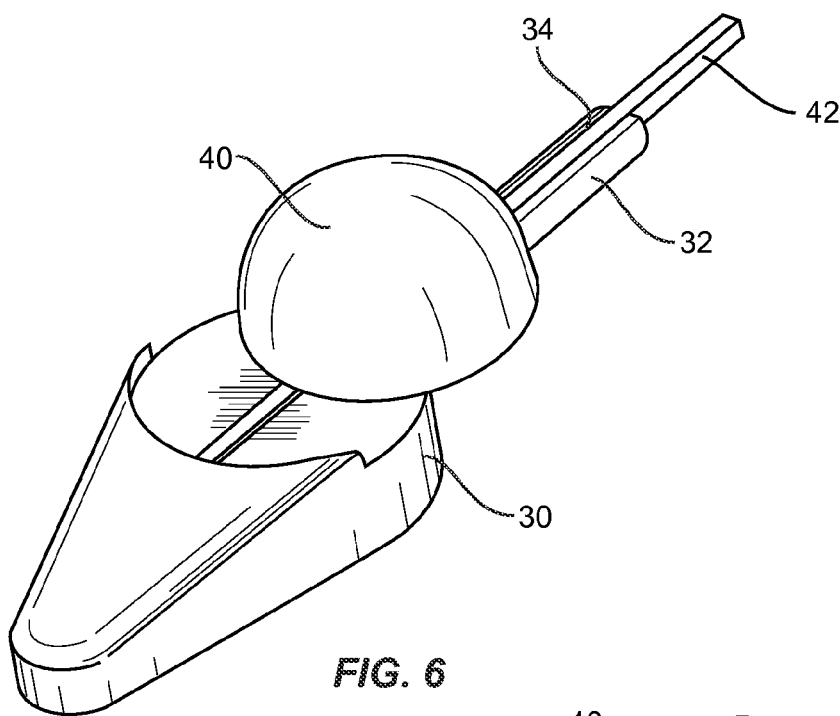
FIG. 6 shows an isometric view illustrating the manner in which the first and second modules of a prosthesis of the present invention cooperate.
Figure 7:
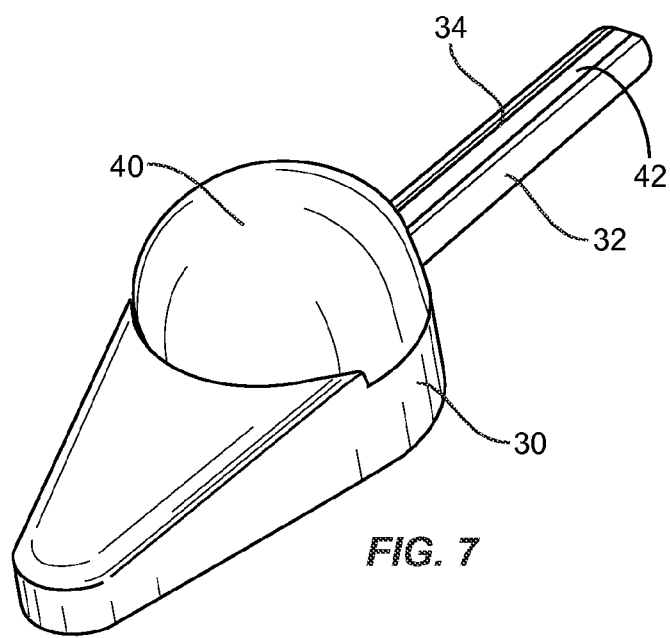
FIG. 7 shows an isometric view illustrating the cooperation of the first and second components of a prosthesis.

In operation, the nucleus pulposus 24 is removed, as necessary, from the disc space 20 in order to accommodate the insertion of a prosthesis 100 according to the present invention. The first module 40 is inserted through the incision 26 in the annulus 22 and into the disc space 20 with the aid of the first insertion rod 32. That is, the distal end 39 passes through the incision 26 and penetrates the disc space 20 first, while the surgeon is holding onto a proximal end (not shown) of the first insertion rod 32, i.e., the end opposite the first component 30. After the first component is in the desired position in the disc space 20, the surgeon then inserts the second component 40 through the incision 26 and into the dis space 20. The surgeon places the second insertion rod 42 into the proximal end of slot 34 and slides the second insertion rod 42 through the slot 34, as shown in FIG. 6, until the second component 40 cooperates with the first component 30 in the disc space 20. As shown in FIG. 7, this is achieved when the second component 40 cooperates or mates with the cut-away portion 35 of the first component 30. In addition, a locking mechanism can be utilized to know when the second component is in its desired position and has properly mated with the first component 30. As examples, a quick connect, snap fit, living hinge or other mechanism may be utilized. For example, as shown in FIG. 5, on the distal end of the second insertion rod 42, there is a slight lip or protrusion 44 that can engage a corresponding hole or gap in slot 34.

Figure 8:
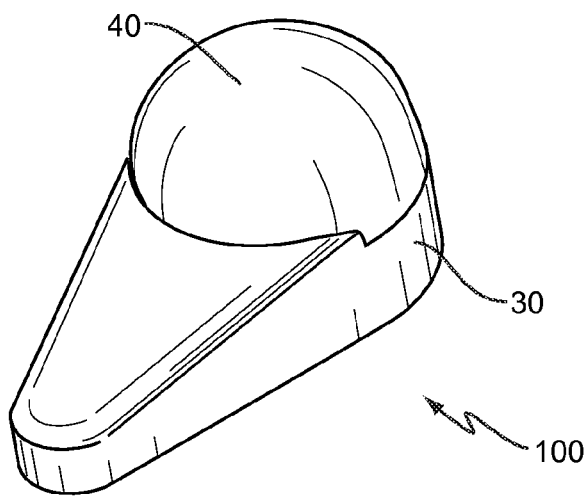
FIG. 8 shows an isometric view of the manner in which the first and second components of a prosthesis cooperate after their respective insertion rods have been detached.

After both the first component 30 and the second component 40 are in desired position in the disc space 20 and properly mated, the insertion rods 32 and 42 may be separated from their respective components or detached in some manner by the surgeon and done in a way that detaches the rods from the components at the respective proximal ends of the components 30 and 40. For example, the insertion rods 32 and 42 may be snapped off from their respective components at their respective proximal ends. Various mechanisms can be used to accomplish this. For example, a perforation type of mechanism at these points will facilitate such a breaking or snapping off of the rods 32 and 42. Thus, after the insertion rods 32 and 42 are separated from their respective components, and the insertion rods 32 and 42 are removed from the disc space and from the body, the prosthesis 100 according to the present invention will remain in the disc space 20. As shown in FIG. 8, the prosthesis includes the first component 30 and the second component 40.

There are various benefits of the prosthesis of FIGS. 4-8. For example, the second component 40 is of a spherical shape to fit in the nuclear recess, i.e., particularly in the caudal-rostral dimension to restore disc height and to re-stabilize the disc space 20 and adjacent vertebrae 12 and 14. This overall spherical shape of the exposed part of the second component 40 also utilizes the endplate geometry for adequate fixation, while retaining motion and even stress distribution in the lateral direction. In addition, the first component 30 allows for a larger foot print on the inferior endplate, which is designed to minimize the extent of subsidence of the prosthesis 100.

Further, with the particular shape of the first component 30, i.e., with the relatively narrow or pointed portion at its distal end 39, the first component 30 is self-distracting to allow for an easy insertion of the first component 30 through the incision 26 and into the disc space 20. In particular, as shown in the figures, the upper surface of the first component 30 has a rise from the relatively narrow or pointy distal end 39 as it moves toward the cut-away portion 35. This can be described as being in the sagittal plane, or in the caudal-rostral dimension. In addition, however, there is an increase in width, or a similar rise, in the direction perpendicular to this one (in the transverse plane). As shown in FIG. 4, for example, component 30 is wider and has a larger angle of inclination in the transverse plane than it does in the sagittal plane. Thus, where more distraction is desired, component 30 can be inserted between the vertebrae when it is turned on its side, or approximately 90 degrees, with respect to the view shown in FIG. 4. With a mostly vertical incision 26 in the annular wall 22, this position also is desirable, as the component 30 would be oriented vertically and therefore could reduce further damage to the annular wall 22. Once in the disc space 20, the component 30 can be turned back "upside right" and assume the position as shown in FIG. 4, i.e., namely that with the lower surface 33 abutting the upper surface or endplate 18 of the inferior vertebra 14.

In addition, the insertion rods 32 and 42 provide for simple, safe and accurate implantation, and even re-positioning of the prosthesis 100 before the rods 32 and 42 are detached. Further, the slot aspect of how the two insertion rods 32 and 42 are designed not only facilitates implanting of the second component 40, but prohibits the two components 30 and 40 from detaching from each other once in proper position in the disc space 20. Also, as demonstrated, the prosthesis 100 of the present invention requires only a relatively small opening (or incision 26) in the annulus 22 so that the prosthesis 100 may be inserted into the disc space 20 by using multiple components, with each having a smaller profile than the final design.

Figure 9:
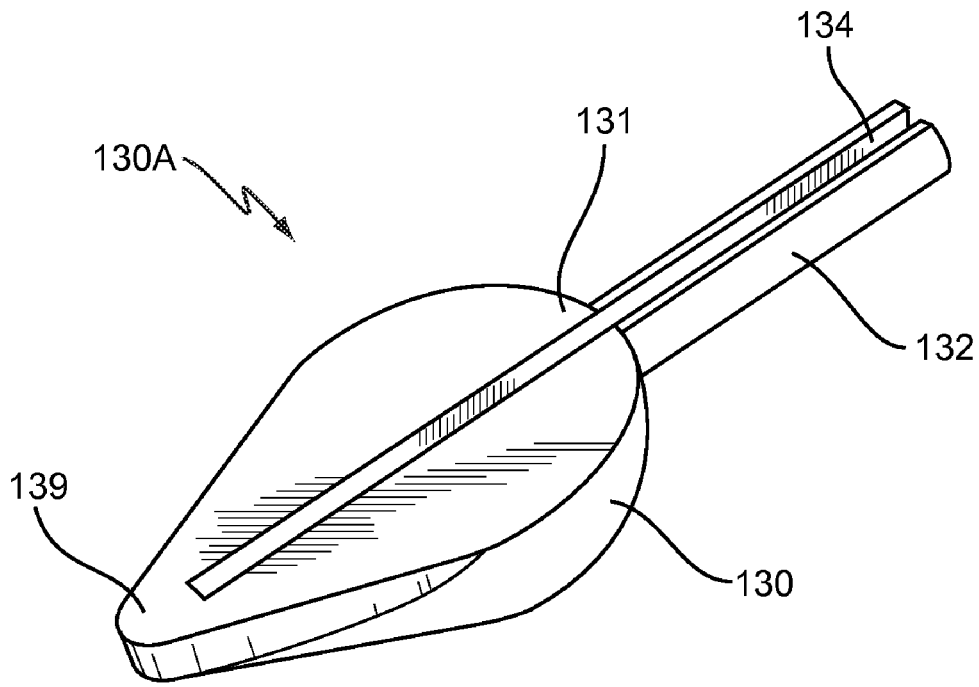
FIG. 9 shows an isometric view of a first module of a second embodiment of a prosthesis according to the present invention.

FIGS. 9-12 show various views of a specially designed prosthesis 200 embodying principles of the present invention. FIG. 9 shows a first module 130A, which comprises a first component 130 and a first insertion rod 132. The first component 130A has a cross section that is generally pear-shaped, having a round portion at its proximal end 131 and a pointed portion at its distal end 139. As opposed to the first component 30A of FIGS. 4-8, however, the first component 130 has a rounded lower surface. In this way, the first component 130 is shaped like half a pear after a whole pear is cut along its longitudinal axis, as shown in FIG. 9. The first insertion rod 132 and the first component 130 has a slot 134 that is co-linear as it extends through the first insertion rod 132 and through the first component 30. As shown in FIG. 9, the slot 134 is centered in the middle of the first insertion rod 132 and in the upper surface of the first insertion rod 132. Similarly, as shown in FIG. 9, the slot 134 is centered in the middle of the first component 30 and along its longitudinal axis, and the slot 134 is continuous through both the first insertion rod 132 and the first component 130.

Figure 10:
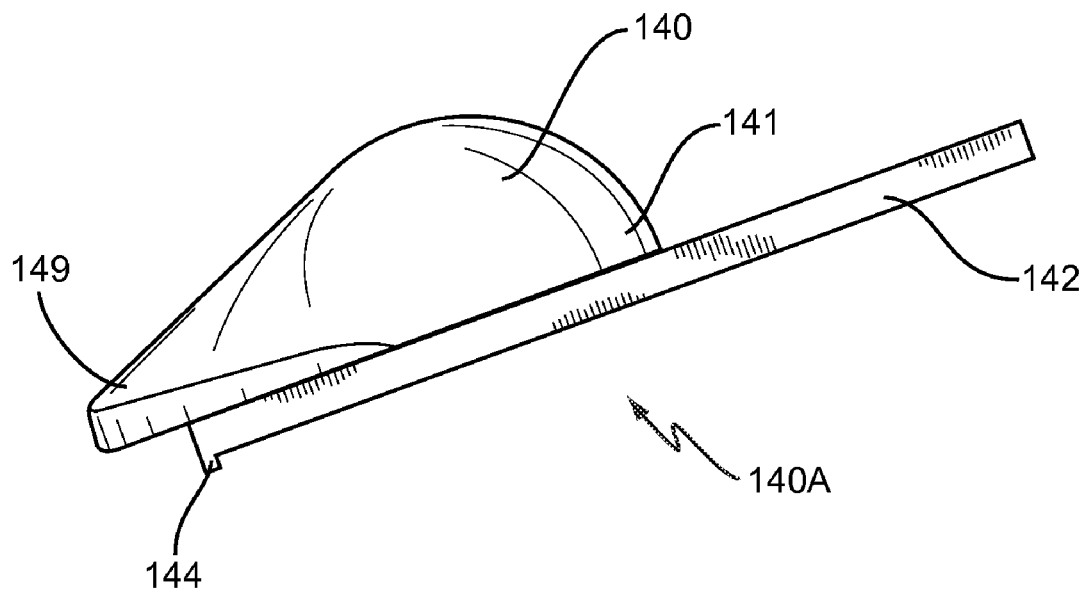
FIG. 10 shows a side view of a second module of the second embodiment of the prosthesis according to the present invention.

FIG. 10 shows a side view of second module 140A, which comprises a second component 140 and a second insertion rod 142. As with the first component 130, the second component 140 has a cross section that is generally pear-shaped, having a round portion at its proximal end 141 and a pointed portion at its distal end 149. Also, the second component 140 has a rounded upper surface. Similar to the first component 130, the second component 140 is shaped like half a pear after a whole pear is cut along its longitudinal axis, as shown in FIG. 10. The second insertion rod 142 is co-linear and continuous as it extends along the base of the second component 140 and extends from the proximal 141 away from the distal end 149 of the second component 140. As shown in FIG. 10, the second insertion rod 142 is centered in the middle of the second component 140 and along its longitudinal axis. Also as shown in FIG. 10, the second insertion rod 142 of second module 140 is shaped so that it can cooperate, or fit within, and slide along slot 134 of first insertion rod 132.

Figure 11:
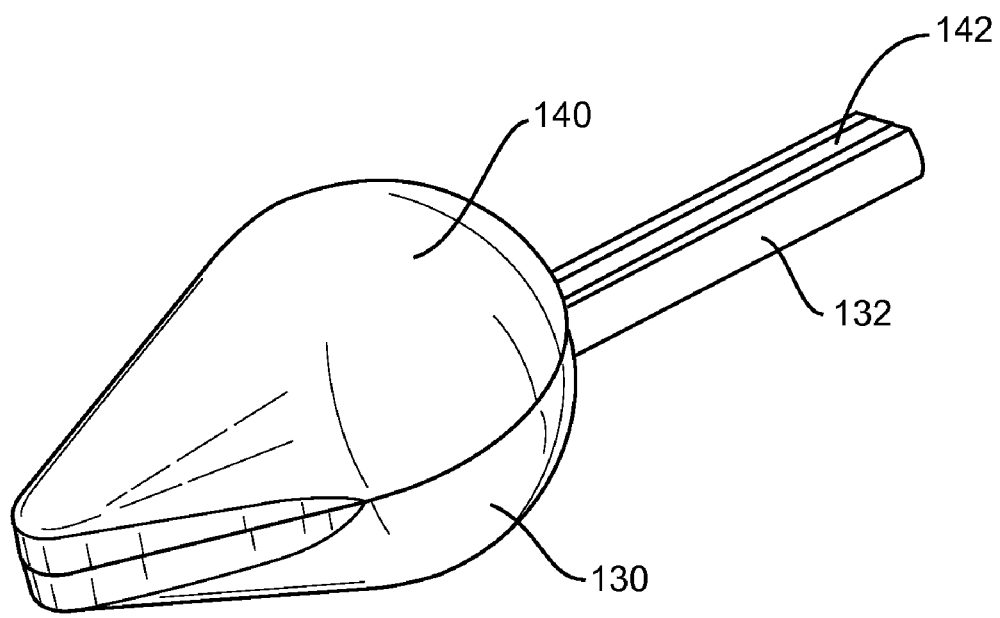
FIG. 11 shows an isometric view illustrating the manner in which the first and second modules of the second embodiment of the prosthesis of the present invention cooperate.

In operation, after the nucleus pulposus 24 is removed, as necessary, from the disc space 20, the first module 130 is inserted through the incision 26 in the annulus 22 and into the disc space 20 with the aid of the first insertion rod 132. That is, the distal end 139 passes through the incision 26 and penetrates the disc space 20 first, while the surgeon is holding onto a proximal end (not shown) of the first insertion rod 132, i.e., end opposite the first component 130. After the first component 130 is in the desired position in the disc space 20, the surgeon then inserts the second component 140 through the incision 26 and into the disc space 20. The surgeon places the second insertion rod 142 into the proximal end of slot 134 and slides the second insertion rod 142 through the slot 134 (similar to that of FIG. 6), until the second component 140 cooperates with the first component 130 in the disc space 20. As shown in FIG. 11, this is achieved when the second component 40 cooperates or mates with the first component 130. In addition, a locking mechanism can be utilized to know when the second component 140 is in its desired position and has properly mated with the first component 130. Examples of such locking mechanisms for prosthesis 200 are similar to those that can be used for prosthesis 100 of FIG. 4-8. For example, as shown in FIG. 10, on the distal end of the second insertion rod 142, there is a slight lip or protrusion 144 that can engage a corresponding hole or gap in slot 134.

Figure 12:
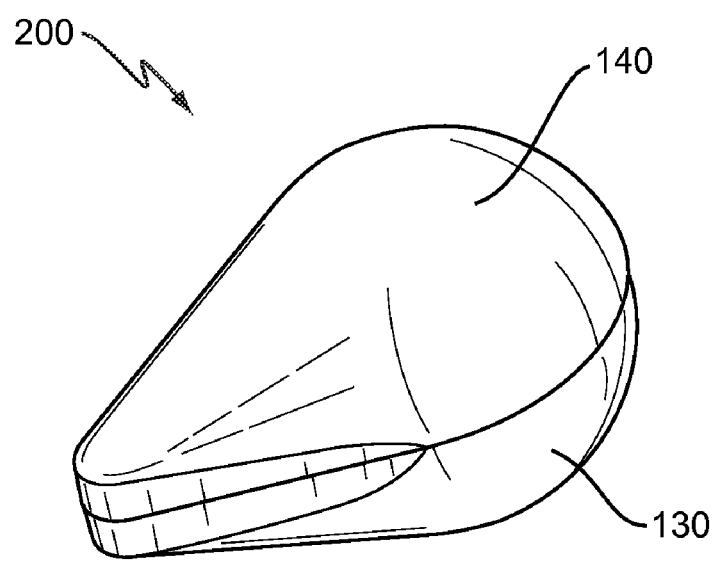
FIG. 12 shows an isometric view of the manner in which the first and second components of the second embodiment of the prosthesis of the present invention cooperate after their respective insertion rods have been detached.

As with the prosthesis 100 of FIG. 4-8A, after both the first component 130 and the second component 140 are in desired position in the disc space 20 and properly mated, the insertion rods 132 and 142 may be snapped off by the surgeon and done in a way that breaks the rods off at the respective proximal ends of the components 130 and 140. A perforation type of mechanism at these points will facilitate such a breaking off of the rods 132 and 142. Thus, after the insertion rods 132 and 142 are separated from their respective components, the prosthesis 200 according to the present invention will remain in the disc space 20. As shown in FIG. 12, the prosthesis includes the first component 130 and the second component 140.

Some of the same benefits of the prosthesis 100 of FIGS. 4-8 are present with the prosthesis 200 of FIGS. 9-12. For example, both second components 130 and 140 are of a spherical shape to fit in the nuclear recess, i.e., particularly in the caudal-rostral dimension to restore disc height and to re-stabilize the disc space 20 and adjacent vertebrae 12 and 14. The overall spherical portion of the prosthesis 200 also utilizes the endplate geometry for adequate fixation, while retaining motion and proper stress distribution in the lateral direction.

In addition, with the particular shape of each component 130 and 140, i.e., with the relatively pointed portion at their respective distal ends, each component 130 and 140 is self-distracting to allow for an easy insertion of the component 130 and 140 through the incision 26 and into the disc space 20. In particular, as shown in the figures, the distal ends of each component 130 and 140 are relatively narrow and rises up to meet the generally spherically-shaped proximal end, thereby giving it a generally pear-shaped appearance. As described above with respect to component 30, where more distraction is desired, either component 130 or 140 can be inserted between the vertebrae when it is turned on its side, or approximately 90 degrees, with respect to the views shown in FIGS. 9 and 10. With a mostly vertical incision 26 in the annular wall 22, this position also is desirable, as the components 130 or 140 would be oriented vertically and therefore could reduce further damage to the annular wall 22. Once in the disc space 20, the components 130 can be turned back "upside right" and assume the positions as shown in FIGS. 9 and 10. With prosthesis 200, however, one may not want to perform this "turning upside right" step until the second component 140 has been inserted. That is, if it is desirable to have a greater amount of distraction when component 140 is inserted, the insertion rods 132 and 142 should align, so one should maintain both components 130 and 140 aligned vertically until both are in the desired position in the disc space 20.

In addition, the insertion rods 132 and 142 provide for simple, safe and accurate implantation, and even re-positioning of the prosthesis 200 before the rods 132 and 142 are detached. Further, the slot aspect of how the two insertion rods 132 and 1142 are designed not only facilitates implanting of the second component 140, but prohibits the two components 130 and 140 from detaching from each other once in proper position in the disc space 20. Also, as demonstrated, the prosthesis 200 of the present invention requires only a relatively small opening (or incision 26) in the annulus 22 so that the prosthesis 200 may be inserted into the disc space 20 by using multiple components, with each having a smaller profile than the final design.

The present invention does not depend on the materials of the constituent parts, but any of the components or modules may be made of any biocompatible materials that are typically used in the intra-discal area. Examples of suitable materials include, but are not limited to, metals such as cobalt-chromium alloys, stainless steels, titanium and titanium alloys. Examples of other materials include, but are not limited to, polymers such as polyetherether ketone ("PEEK"), polyether ketone ("PEK"), polyethylene, and polyurethanes. In addition, various ceramics, biologics and resorbable materials also could be used. Also, a portion of a component or module can be made of a different material than the remainder of the component or module such that the prosthesis can have variable stiffness. Similarly, parts of certain components or modules that occupy the central area of a prosthesis 100 or 200 can be made of a compressible material to provide different load bearing characteristics.

Although only a few exemplary embodiments have been described in detail above, those skilled in the art will readily appreciate that many modifications are possible in the exemplary embodiments without materially departing from the novel teachings and advantages of this disclosure. An example of such a modification would be modifying the overall shape of prosthesis 100 or 200, and/or using more than two components to create a prosthesis 100 or 200. That is, a prosthesis according to the principles of the present invention may be made with more than two constituent components. For example, multiple slots also may be utilized.

Accordingly, all such adjustments and alternatives are intended to be included within the scope of the invention, as defined exclusively in the following claims. Those skilled in the art should also realize that such modifications and equivalent constructions or methods do not depart from the spirit and scope of the present disclosure, and that they may make various changes, substitutions, and alternations herein without departing from the spirit and scope of the present disclosure. Furthermore, as used herein, the terms components and modules may be interchanged. It is understood that all spatial references, such as "anterior," "posterior," "inward," "outward," and "sides" are for illustrative purposes only and can be varied within the scope of the disclosure.

The invention claimed is:

1. An intervertebral prosthesis system for implanting an intervertebral prosthesis within a disc space and disposed between upper and lower vertebral endplates, the prosthesis system comprising:
a plurality of prosthesis components comprising a first component with a pear-shaped cross-sectional configuration and a second component with a hemispherical shaped configuration, the pear-shaped cross-sectional configuration of the first component being formed by a substantially triangular-shaped first portion having an arcuate upper surface, said first portion abutting a circular second portion including a planar upper surface, the upper surface of the second portion being recessed relative to the upper surface of the first portion such that a lower surface of the second component engages the upper surface of the second portion of the first component without engaging the arcuate upper surface of the first portion of the first component, the plurality of components being insertable into the disc space, wherein:
the components have surfaces configured to engage within the disc space in a manner such that the components form an assembled prosthesis of a size substantially preventing it from being outwardly expelled from the disc space through an opening in the disc space;
the components have bearing surfaces slidably engageable with the endplates to permit articulation between upper and lower vertebral endplates; and
the components each have an insertion rod attached to the component for inserting the respective component to which the insertion rod is attached into the disc space.

2. The intervertebral prosthesis system of claim 1, wherein a first insertion rod of the first component has a slot in which at least a second insertion rod of the second component can be inserted and used to guide the at least second component into the disc space.

3. The intervertebral prosthesis of claim 1, wherein each of the insertion rods are configured such that each can be detached from their respective components.

4. The intervertebral prosthesis of claim 1, wherein the first component comprises a slot and the second component comprises an insertion rod that fits in the slot.

5. The intervertebral prosthesis system of claim 1, wherein the prosthesis is configured such that in its final shape, it has a lower surface that is relatively flat.

6. The intervertebral prosthesis of claim 1, wherein the prosthesis is configured such that in its final shape, it is shaped like half a pear after a whole pear is cut along a longitudinal axis of the whole pear.

7. The intervertebral prosthesis of claim 1, wherein the prosthesis is configured such that in its final shape, the plurality of components are locked together with a locking mechanism.

8. The intervertebral prosthesis of claim 1, wherein when the prosthesis is in its final shape, the plurality of components are locked together with a locking mechanism.

9. The intervertebral prosthesis of claim 1, wherein an interface between the first and second portion defines a lip, and an exterior surface of the second component engages the lip to fix the position of the second component relative to the first component.

10. The intervertebral prosthesis of claim 1, wherein a first insertion rod of the first component has a slot in which at least a second insertion rod of the second component can be inserted and used to guide the at least second component into the disc space, a first end of the second insertion rod comprises a protrusion extending transversely therefrom configured for disposal in a first end of the first insertion rod to prevent the first insertion rod from moving relative to the second insertion rod.

11. A method of implanting an intervertebral prosthesis within a disc space between upper and lower vertebral endplates, the method comprising:
providing an intervertebral prosthesis system for implanting an intervertebral prosthesis within a disc space and disposed between upper and lower vertebral endplates, the prosthesis system comprising:
a plurality of prosthesis components comprising a first component with a pear-shaped cross-sectional configuration and a second component with a hemispherical shaped configuration, the pear-shaped cross-sectional configuration of the first component being formed by a substantially triangular-shaped first portion having an arcuate upper surface, said first portion abutting a circular second portion including a planar upper surface, the upper surface of the second portion being recessed relative to the upper surface of the first portion such that a lower surface of the second component engages the upper surface of the second portion of the first component without engaging the arcuate upper surface of the first portion of the first component, the plurality of components being insertable into the disc space, wherein:
the components have surfaces configured to engage within the disc space in a manner such that the components form an assembled prosthesis of a size substantially preventing it from being outwardly expelled from the disc space through an opening in the disc space;
the components have bearing surfaces slidably engageable with the endplates to permit articulation between upper and lower vertebral endplates; and
the components each have an insertion rod attached to the component for inserting the respective component to which the insertion rod is attached into the disc space;
using the insertion rod of the first component to insert the first component through an incision in an annular wall and into the disc space;
using the insertion rod of the second component to insert the second component through the incision in the annular wall and into the disc space; and
after the first component and second component are in their respective final positions in the disc space, detaching the first and second insertion rods from their respective components.

12. The method of implanting an intervertebral prosthesis of claim 11, wherein prior to insertion through the annular wall and into the disc space, the method further comprises rotating at least one of the components approximately 90 degrees so that the at least one component is inserted through the incision and into the disc space in a vertical position.

13. The method of implanting an intervertebral prosthesis of claim 11, wherein the insertion rod of the first component has a slot and the insertion rod of the second component fits in the slot to enable the second component to cooperate with the first component and be guided into proper location in the disc space.

\* \* \* \* \*